(12) United States Patent  (10) Patent No.: US 7,364,756 B2
Gabbay  (45) Date of Patent: Apr. 29, 2008

(54) ANTI-VIRUS HYDROPHILIC POLYMERIC MATERIAL

(75) Inventor: Jeffrey Gabbay, Jerusalem (IL)

(73) Assignee: The Cuprin Corporation, New York, NY (US)

( * ) Notice: Subject to any disclaimer, the term of this patent is extended or adjusted under 35 U.S.C. 154(b) by 339 days.

(21) Appl. No.: 10/772,890

(22) Filed: Feb. 4, 2004

(65) Prior Publication Data

US 2005/0048131 A1 Mar. 3, 2005

Related U.S. Application Data

(63) Continuation-in-part of application No. 10/752,938, filed on Jan. 6, 2004, now abandoned.

(30) Foreign Application Priority Data

Aug. 28, 2003 (IL) ...................................... 157625

(51) Int. Cl.
A61K 33/34 (2006.01)
A61K 31/74 (2006.01)
A01N 25/34 (2006.01)
(52) U.S. Cl. .................... 424/635; 424/78.08; 424/404
(58) Field of Classification Search ................ 424/635, 424/78.08, 404
See application file for complete search history.

(56) References Cited

U.S. PATENT DOCUMENTS

| | | | |
|---|---|---|---|
| 252,524 A | 1/1882 | Sagendorph |
| 1,210,375 A | 12/1916 | Decker |
| 3,014,818 A | 12/1961 | Campbell |
| 3,308,488 A | 3/1967 | Schoonman |
| 3,385,915 A | 5/1968 | Hamling |
| 3,663,182 A | 5/1972 | Hamling |
| 3,769,060 A | 10/1973 | Ida et al. |
| 3,821,163 A | 6/1974 | Spivack |
| 3,860,529 A | 1/1975 | Hamling |
| 4,072,784 A | 2/1978 | Cirino et al. |
| 4,103,450 A | 8/1978 | Whitcomb |
| 4,115,422 A | 9/1978 | Welch et al. |
| 4,174,418 A | 11/1979 | Welch et al. |
| 4,201,825 A | 5/1980 | Ebneth |
| 4,219,602 A | 8/1980 | Conklin |
| 4,278,435 A | 7/1981 | Ebneth |
| 4,291,086 A | 9/1981 | Auten |
| 4,292,882 A | 10/1981 | Clausen |
| 4,317,856 A | 3/1982 | Huthwelker et al. |
| 4,366,202 A | 12/1982 | Borovsky |
| 4,390,585 A | 6/1983 | Holden |
| 4,525,410 A | 6/1985 | Hagiwara et al. |
| 4,666,940 A | 5/1987 | Bischoff et al. |
| 4,675,014 A | 6/1987 | Sustmann et al. |
| 4,710,184 A | 12/1987 | Ehret |
| 4,769,275 A | 9/1988 | Inagaki et al. |
| 4,853,019 A | 8/1989 | Blank et al. |
| 4,900,618 A | 2/1990 | O'Connor et al. |
| 4,900,765 A | 2/1990 | Murabayshi et al. |
| 4,983,573 A | 1/1991 | Bolt et al. |
| 4,999,240 A | 3/1991 | Brotz |
| 5,009,946 A | 4/1991 | Hatomoto et al. |
| 5,017,420 A | 5/1991 | Marikar et al. |
| 5,024,875 A | 6/1991 | Hill et al. |
| 5,066,538 A | 11/1991 | Huykman |
| 5,143,769 A | 9/1992 | Moriya et al. |
| 5,175,040 A | 12/1992 | Harpell et al. |
| 5,180,585 A * | 1/1993 | Jacobson et al. ........... 424/405 |
| 5,200,256 A | 4/1993 | Dunbar |
| 5,217,626 A | 6/1993 | Yahya et al. |
| 5,227,365 A | 7/1993 | Van den Sype |
| 5,254,134 A | 10/1993 | Zhao et al. |
| 5,269,973 A | 12/1993 | Takahashi et al. |
| 5,316,837 A | 5/1994 | Cohen |
| 5,316,846 A | 5/1994 | Pinsky et al. |
| 5,370,934 A | 12/1994 | Burch et al. |
| 5,399,425 A | 3/1995 | Burch |
| 5,405,644 A | 4/1995 | Ohsumi et al. |
| 5,407,743 A | 4/1995 | Clough et al. |
| 5,411,795 A | 5/1995 | Silverman |
| 5,458,906 A | 10/1995 | Liang |
| 5,492,882 A | 2/1996 | Doughty et al. |

(Continued)

FOREIGN PATENT DOCUMENTS

DE 4403016 A1 8/1995

(Continued)

OTHER PUBLICATIONS

US Patent Application as filed, U.S. Appl. No. 10/240,993, filed Oct. 4, 2004.

(Continued)

Primary Examiner—Shelley A. Dodson
(74) Attorney, Agent, or Firm—Townsend and Townsend and Crew LLP

(57) ABSTRACT

The invention provides a method for imparting antiviral properties to a hydrophilic polymeric material comprising preparing a hydrophilic polymeric slurry, dispersing an ionic copper powder mixture containing cuprous oxide and cupric oxide in said slurry and then extruding or molding said slurry to form a hydrophilic polymeric material, wherein water-insoluble particles that release both $Cu^{++}$ and $Cu^{+}$ are directly and completely encapsulated within said hydrophilic polymeric material.

14 Claims, 2 Drawing Sheets

U.S. PATENT DOCUMENTS

Figure 1:
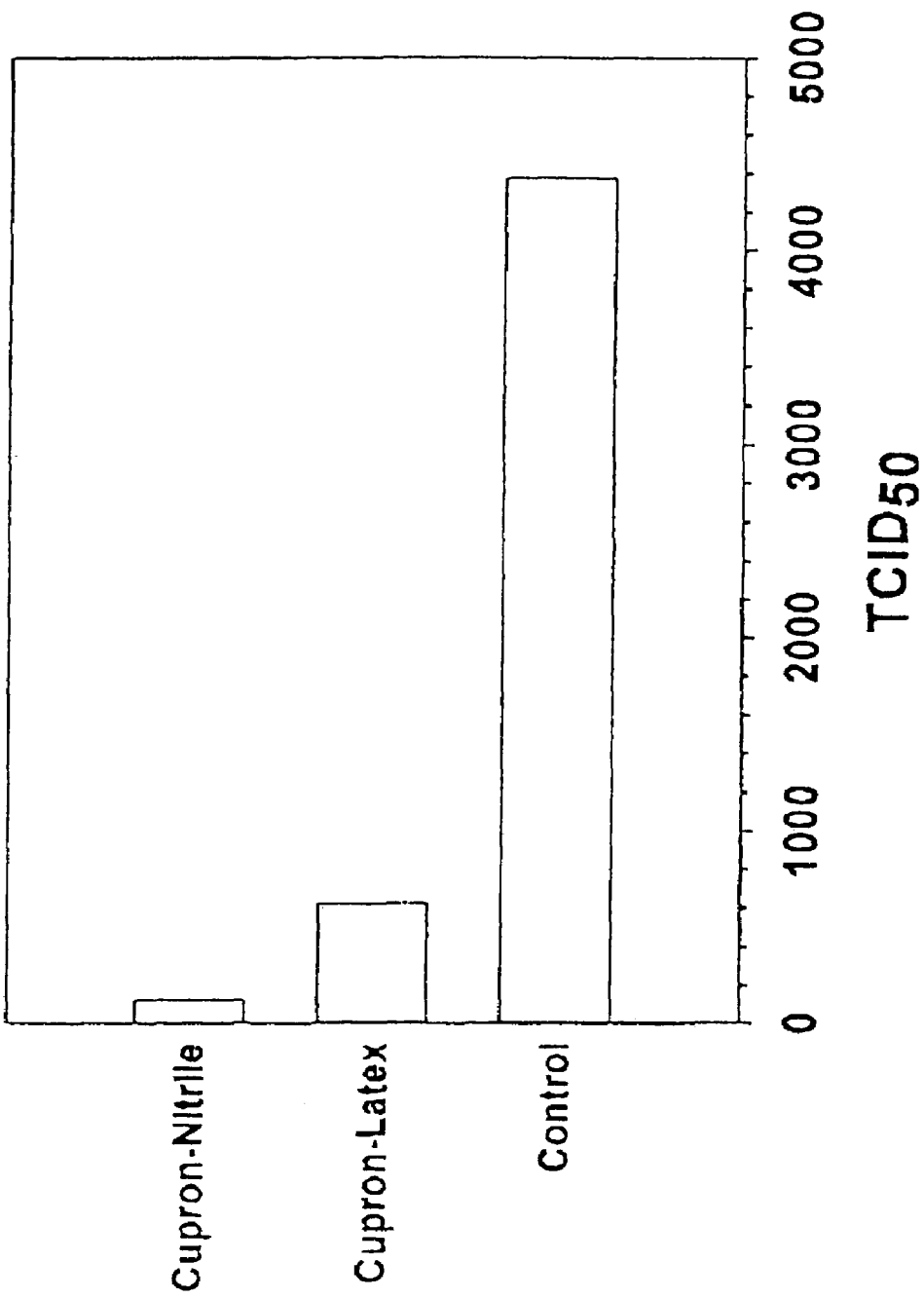

| | | | |
|---|---|---|---|
| 5,518,812 A | 5/1996 | Mitchnick et al. | |
| 5,547,610 A | 8/1996 | Mortensen | |
| 5,549,972 A | 8/1996 | Hsu et al. | |
| 5,744,222 A | 4/1998 | Sugihara | |
| 5,848,592 A | 12/1998 | Sibley | |
| 5,849,235 A | 12/1998 | Sassa et al. | |
| 5,856,248 A | 1/1999 | Weinberg | |
| 5,869,412 A | 2/1999 | Yenni, Jr. et al. | |
| 5,871,816 A | 2/1999 | Tal | |
| 5,881,353 A | 3/1999 | Kamigata et al. | |
| 5,904,854 A | 5/1999 | Shmidt et al. | |
| 5,939,340 A | 8/1999 | Gabbay | |
| 5,981,066 A | 11/1999 | Gabbay | |
| 6,013,275 A | 1/2000 | Konagaya et al. | |
| 6,124,221 A | 9/2000 | Gabbay | |
| 6,383,273 B1 | 5/2002 | Kepner et al. | |
| 6,394,281 B2 | 5/2002 | Ritland et al. | |
| 6,482,424 B1 | 11/2002 | Gabbay | |
| 7,169,402 B2 * | 1/2007 | Gabbay | 424/404 |
| 2004/0247653 A1 * | 12/2004 | Gabbay | 424/443 |

FOREIGN PATENT DOCUMENTS

| | | |
|---|---|---|
| EP | 116 825 | 8/1984 |
| EP | 253 653 | 1/1989 |
| EP | 427 858 | 5/1991 |
| FR | 1499358 A | 9/1967 |
| FR | 2764518 | 6/1997 |
| GB | 415213 | 8/1934 |
| GB | 1382820 | 12/1971 |
| JP | 63-088007 | 4/1988 |
| JP | 01-046465 | 2/1989 |
| JP | 01-246204 | 10/1989 |
| JP | 02-161954 | 6/1990 |
| JP | 03-113011 | 5/1991 |
| JP | 06-285772 | 5/1996 |
| WO | WO 94/15463 | 7/1994 |
| WO | WO 98/06508 | 2/1998 |
| WO | WO 98/06509 | 2/1998 |
| WO | WO 00/75415 | 12/2000 |
| WO | WO 01/74166 | 10/2001 |
| WO | WO 01/81671 | 11/2001 |

OTHER PUBLICATIONS

US Patent Application as filed, U.S. Appl. No. 10/339,886, filed Jan. 10, 2003.

US Patent Application as filed, U.S. Appl. No. 10/405,408, filed Apr. 1, 2003.

US Patent Application as filed, U.S. Appl. No. 10/371,491, filed Feb. 21, 2003.

US Patent Application as filed, U.S. Appl. No. 10/757,786, filed Jan. 13, 2004.

US Patent Application as filed, U.S. Appl. No. 10/756,849, filed Jan. 13, 2004.

US Patent Application as filed, U.S. Appl. No. 10/133,691, filed Apr. 24, 2002.

US Patent Application as filed, U.S. Appl. No. 10/752,938, filed Jan. 6, 2004.

US Patent Application as filed, U.S. Appl. No. 10/772,890, filed Feb. 4, 2004.

"Encyclopedia of Polymer Science and Technology," John Wiley & Sons, Inc., (1968) vol. 8, pp. 651-666 and vol. 9, pp. 580-598.

Marino, A. et al., "Electrochemical Properties of Silver-Nylon Fabrics," J. Electrochem. Soc. (1985) vol. 132, No. 1, pp. 68-72.

* cited by examiner

ANTI-VIRUS HYDROPHILIC POLYMERIC MATERIAL

This application is a continuation-in-part application of U.S. Ser. No. 10/752,938, filed Jan. 6, 2004 which claims priority under 35 USC §119 to Israel patent application no. 157,625 filed Aug. 28, 2003, both of which are herein incorporated by reference in their entirety for all purposes.

The present invention relates to a method for imparting antiviral properties to a hydrophilic polymeric material, to hydrophilic polymeric materials for inactivation of a virus and to devices incorporating the same.

More particularly, the present invention relates to hydrophilic polymeric materials incorporating a mixture of water-insoluble particles that release both $Cu^{++}$ and $Cu^+$ wherein said particles are directly and completely encapsulated within said hydrophilic polymeric material.

In especially preferred embodiments, the present invention relates to a multi-layered hydrophilic polymeric material incorporating a mixture of water-insoluble particles that release both $Cu^{++}$ and $Cu^+$.

In WO 01/74166 there is described and claimed an antimicrobial and antiviral polymeric material, having microscopic particles of ionic copper encapsulated therein and protruding from surfaces thereof and the relevant teachings of said publication are incorporated herein by reference.

In said publication it is indicated that the polymeric material can be any synthetic polymer and examples which are mentioned are polyamides (nylon), polyester, acrylic, polypropylene, silastic rubber and latex.

As will be noted however, Example 1 of said patent related to the preparation of a polyamide bi-component compound into which the copper powder was added and the tests for antiviral, antifungal and antibacterial activity were carried out with said fibers.

In Example 4 of said patent, latex gloves were prepared however these were made from latex having microscopic particles of ionic copper protruding from the surfaces thereof.

At the time of the writing of said specification it was believed that all of the polymeric materials listed therein were effective as antimicrobial and antiviral only when the microscopic particles of ionic copper were protruding from the surfaces of the polymeric material as seen e.g. in FIG. 1 of said publication.

According to the present invention it has now been surprisingly discovered that when working with a hydrophilic polymeric material it is possible to produce a material and devices based thereon that possess antiviral properties even though the particles that release both $Cu^{++}$ and $Cu^+$ are directly and completely encapsulated within said hydrophilic polymeric material.

In light of this surprising discovery which is neither taught nor suggested in said earlier specification, there is now provided according to the present invention a method for imparting antiviral properties to a hydrophilic polymeric material comprising preparing a hydrophilic polymeric slurry, dispersing an ionic copper powder mixture containing cuprous oxide and cupric oxide in said slurry and then extruding or molding said slurry to form a hydrophilic polymeric material, wherein water-insoluble particles that release both $Cu^{++}$ and $Cu^+$ are directly and completely encapsulated within said hydrophilic polymeric material.

In preferred embodiments of the present invention said ionic copper powder mixture is prepared by oxidation-reduction and preferably in the preparation of said ionic copper powder said reduction is carried out using formaldehyde as a reductant.

The invention also provides a hydrophilic polymeric material for inactivation of a virus comprising a mixture of water-insoluble particles that release both $Cu^{++}$ and $Cu^+$, which particles are directly and completely encapsulated within said hydrophilic polymeric material and are the primary active component therein.

In preferred embodiments of the present invention said particles are of a size of between about 1 and 10 microns and preferably said particles are present within said hydrophilic material in a concentration of about 1 to 3 w/w %.

As indicated the present invention is specifically directed to imparting antiviral properties to a hydrophilic polymeric material and in preferred embodiments of the present invention said hydrophilic polymeric material is selected from the group consisting of latex, nitrile, acrylics, polyvinyl alcohol and silastic rubber.

According to the present invention there is also provided a thin hydrophilic polymeric coating comprising said mixture of water-insoluble particles that release both $Cu^{++}$ and $Cu^+$, which particles are directly and completely encapsulated within said hydrophilic polymeric coating material and are the primary active component therein.

Such thin layer coatings can be applied on polymeric and other substrates and is especially useful for application to polymers, the polymerization of which might be disrupted by the presence of cationic species of copper and or for the coating of latex polymeric articles wherein sensitivity to latex is problematic, such as in latex gloves and condoms.

Based on the findings of the present invention it is now possible and the present invention also provides a device for the inactivation of a virus brought in contact therewith, wherein said device is in the form of a nipple or nipple shield formed from a hydrophilic polymeric material comprising a mixture of water-insoluble particles that release both $Cu^{++}$ and $Cu^+$, which particles are directly and completely encapsulated within said hydrophilic polymeric material.

The invention also provides a device for the inactivation of a virus brought in contact therewith, wherein said device is in the form of a bag formed from a hydrophilic polymeric material comprising a mixture of water-insoluble particles that release both $Cu^{++}$ and $Cu^+$, which particles are directly and completely encapsulated within said hydrophilic polymeric material and preferably said bag is a blood storage bag.

In further preferred embodiments of the present invention there is provided a device for the inactivation of a virus brought in contact therewith, wherein said device is in the form of a tube formed from a hydrophilic polymeric material comprising a mixture of water-insoluble particles that release both $Cu^{++}$ and $Cu^+$, which particles are directly and completely encapsulated within said hydrophilic polymeric material.

Preferably said tube is a tube for transfer of body fluids such as blood or milk.

In especially preferred embodiments of said device of the present invention said tube is provided with projections extending into the lumen thereof in order to cause mixing of the fluid flowing therethrough to assure contact of all of said fluid with surfaces of said polymeric material.

In a further aspect of the present invention there is provided a device for the inactivation of a virus brought in contact therewith, wherein said device is in the form of a condom formed from a hydrophilic polymeric material comprising a mixture of water-insoluble particles that release both $Cu^{++}$ and $Cu^+$, which particles are directly and completely encapsulated within said hydrophilic polymeric material and are the primary active component therein.

In yet another aspect of the present invention there is provided a device for the inactivation of a virus brought in contact therewith, wherein said device is in the form of a diaphragm formed from a hydrophilic polymeric material comprising a mixture of water-insoluble particles that release both $Cu^{++}$ and $Cu^+$, which particles are directly and completely encapsulated within said hydrophilic polymeric material.

The invention also provides a device for the inactivation of a virus brought in contact therewith, wherein said device is in the form of a glove formed from a hydrophilic polymeric material comprising a mixture of water-insoluble particles that release both $Cu^{++}$ and $Cu^+$, which particles are directly and completely encapsulated within said hydrophilic polymeric material.

The invention also provides a device for the inactivation of a virus brought in contact therewith, wherein said device is in the form of a glove formed from a hydrophilic polymeric material and coated with a thin layer of a further hydrophilic polymeric material, said further hydrophilic polymeric material comprising a mixture of water-insoluble particles that release both $Cu^{++}$ and $Cu^+$, which particles are directly and completely encapsulated within said hydrophilic polymeric material.

In especially preferred embodiments of the present invention there is provided a hydrophilic polymeric material for inactivation of a virus comprising a mixture of water-insoluble particles that release both $Cu^{++}$ and $Cu^+$, which particles are directly and completely encapsulated within said hydrophilic polymeric material and are the sole antiviral component therein.

In U.S. patent application Ser. No. 10/339,886 corresponding to PCT/IL03/00230, the relevant teachings of which are also incorporated herein by reference there is described and claimed a device for the inactivation of a virus comprising a filtering material, said device having ionic copper selected from the group consisting of $Cu^+$ and $Cu^{++}$ ions and combinations thereof incorporated therein.

In said specification there is described the plating of cellulose fibers using a copper solution which results in the formation of copper oxide on the surface of said fibers wherein the process used yields both a Cu(I) and a Cu(II) species as part of a copper oxide molecule. Said fibers were then incorporated into a filter which was found to be effective in the inactivation of HIV-1. Further tests with said filter revealed that this combination was also effective in the inactivation of West Nile fever virus and the neutralization of adenovirus and therefore it is believed that the antiviral hydrophilic polymeric materials of the present invention are also effective against such viruses since they work on the same mechanism.

While the mechanism of the hydrophilic polymeric materials according to the present invention is not fully understood, in light of the results obtained, it is believed that when the polymeric material is brought into contact with a fluid aqueous medium, said medium leaches the cationic species of copper from within said polymer and as described in PCT/IL03/00230 the antiviral activity takes advantage of the redox reaction of the cationic species with water and allows a switch between Cu(II) and Cu(I) when there is contact with water. Cu(I) is more effective than Cu(II) against HIV while Cu(II) is more stable than Cu(I). The Cu(II) compound will oxidize much more slowly than the Cu(I) compound and will increase the shelf life of the product.

As will be realized, in light of the now proven efficacy of cupric ions in the inactivation of HIV, as more fully described in PCT/IL03/00230, the hydrophilic polymeric materials of the present invention can also be used for the solution of at least two major HIV problems which are plaguing the world.

The first of these problems is that in that in the third world countries and especially in African countries entire populations are being decimated by HIV due to the transmission of HIV from infected mothers to their newborn babies via nursing milk.

Due to the poverty prevalent in these countries milk substitutes are not available to newborn and nursing babies and infected mother's milk has been found to be the major cause of transmission of HIV to children.

A further acute problem which also exists in the Western world is the fear of transfusion of HIV contaminated blood.

While blood banks now screen donated blood for HIV antibodies it is known that the test for antibodies is only effective after the incubation period of 60-90 days and therefore there is always the danger that this screening process will not detect the blood of an individual who only contracted HIV within 2 or 3 months of the donation.

Thus, as described hereinbefore, the present invention provides tubes for the transfer of blood and bags for the storage of blood, the surfaces of which are effective for inactivating viruses such as HIV virus. Furthermore, the present invention provides nipples which can be used in breast shields of nursing mothers wherein milk passing therethrough will undergo inactivation of any HIV virus contained therein.

It will be realized that the device and method of the present invention is not limited to the above mentioned preferred uses and that the device can also be used in a hospital or field hospital setting wherein blood from a blood bank is not available and a direct transfusion is mandated in that the preferred tubes of the present invention are provided with projections extending into the lumen thereof in order to cause mixing of the fluid flowing therethrough to assure contact of all of said fluid with surfaces of said polymeric material and thereby blood can be transferred through said tubes which would inactivate any viruses contained in said blood.

In further embodiments of the present invention the devices of the present invention can also be used to inactivate other viruses found in body fluids including the inactivation of West Nile fever which has now been discovered to exist in the blood of carriers of said disease who do not show symptoms thereof however whose blood could contaminate blood banks by transmission of said virus thereto.

As will be realized, once the water insoluble ionic copper compounds are mixed into a hydrophilic polymeric slurry, said slurry can be molded or extruded to form fibers, yarns, films, tubes, sheaths, bags, etc. wherein the water-insoluble particles that release both $Cu^{++}$ and $Cu^+$ are directly and completely encapsulated within said hydrophilic polymeric material.

Unlike the fibers described, e.g. in WO 98/06508 and WO 98/06509, in which the fibers are coated on the outside, in the present product the polymer has microscopic water insoluble particles of ionic copper directly and completely encapsulated therein. These fully encapsulated particles have been shown to be active, as demonstrated by the tests set forth hereinafter.

In WO 94/15463 there are described antimicrobial compositions comprising an inorganic particle with a first coating providing antimicrobial properties and a second coating providing a protective function wherein said first coating can be silver or copper or compounds of silver, copper and zinc and preferred are compounds containing silver and copper (II) oxide. Said patent, however, is based on the complicated and expensive process involving the coating of the metallic compositions with a secondary protective coating selected from silica, silicates, borosilicates, aluminosilicates, alumina, aluminum phosphate, or mixtures thereof and in fact all the claims are directed to compositions having successive coatings including silica, hydrous alumina and dioctyl azelate.

In contradistinction, the present invention is directed to the use and preparation of a hydrophilic polymeric material, wherein water-insoluble particles that release both $Cu^{++}$ and $Cu^+$ are directly and completely encapsulated within said hydrophilic polymeric material which is neither taught nor suggested by said publication and which has the advantage that the $Cu^{++}$ and $Cu^+$ releasing water insoluble particles have been proven to be effective even in the inhibition of HIV-1 activity.

In EP 427858 there is described an antibacterial composition characterized in that inorganic fine particles are coated with an antibacterial metal and/or antibacterial metal compound and said patent does not teach or suggest a hydrophilic polymeric material, wherein water-insoluble particles that release both $Cu^{++}$ and $Cu^+$ are directly and completely encapsulated within said hydrophilic polymeric material.

In DE 4403016 there is described a bacteriacidal and fungicidal composition utilizing copper as opposed to ionic $Cu^{++}$ and $Cu^+$ and said patent also does not teach or suggest a hydrophilic polymeric material, wherein water-insoluble particles that release both $Cu^{++}$ and $Cu^+$ are directly and completely encapsulated within said hydrophilic polymeric material.

In JP-01 046465 there is described a condom releasing sterilizing ions utilizing metals selected from copper, silver, mercury and their alloys which metals have a sterilizing and sperm killing effect, wherein the metal is preferably finely powdered copper. While copper salts such as copper chloride, copper sulfate and copper nitrate are also mentioned as is known these are water soluble salts which will dissolve and break down the polymer in which they are introduced. Similarly, while cuprous oxide is specifically mentioned this is a $Cu^+$ ionic form and therefore said patent does not teach or suggest the use of a hydrophilic polymeric material, wherein water-insoluble particles that release both $Cu^{++}$ and $Cu^+$ are directly and completely encapsulated within said hydrophilic polymeric material, which has been proven to be effective even in the inhibition of HIV-1 activity.

In JP-01 246204 there is described an antimicrobial moulded article in which a mixture of a powdery copper compound and organic polysiloxane are dispersed into a thermoplastic moulded article for the preparation of cloth, socks, etc. Said patent specifically states and teaches that metal ions cannot be introduced by themselves into a polymer molecule and requires the inclusion of organopolysiloxane which is also intended to provide a connecting path for the release of copper ions to the fiber surface. Thus, as will be realized said copper compound will be encapsulated and said patent does not teach or suggest the use of a hydrophilic polymeric material, wherein water-insoluble particles that release both $Cu^{++}$ and $Cu^+$ are directly and completely encapsulated within said hydrophilic polymeric material.

In JP-03 113011 there is described a fiber having good antifungus and hygienic action preferably for producing underwear wherein said synthetic fiber contains copper or a copper compound in combination with germanium or a compound thereof, however, said patent teaches and requires the presence of a major portion of germanium and the copper compounds disclose therein are preferably metallic copper, cuprous iodide which is a monovalent $Cu^+$ compound and water soluble copper salts. Thus, said patent does not teach or suggest the use of a hydrophilic polymeric material, wherein water-insoluble particles that release both $Cu^{++}$ and $Cu^+$ are directly and completely encapsulated within said hydrophilic polymeric material.

In EP 116865 there is described and claimed a polymer article containing zeolite particles at least part of which retain at least one metal ion having a bacterial property and thus said patent does not teach or suggest the use of $Cu^{++}$ and $Cu^+$ releasing water insoluble particles, by themselves and in the absence of a zeolite, which have been proven to be effective even in the inhibition of HIV-1 activity.

In EP 253653 there is described and claimed a polymer containing amorphous aluminosilicate particles comprising an organic polymer and amorphous aluminosilicate solid particles or amorphous aluminosilicate solid particles treated with a coating agent, at least some of said amorphous aluminosilicate solid particles holding metal ions having a bactericidal actions. Thus, said patent does not teach or suggest the use of $Cu^{++}$ and $Cu^+$ releasing water insoluble particles, by themselves and in the absence of amorphous aluminosilicate particles, which have been proven to be effective even in the inhibition of HIV-1 activity.

As indicated hereinabove, the hydrophilic polymeric material of the present invention, having microscopic particles of ionic copper directly and completely encapsulated therein, can also be utilized to manufacture disposable gloves and condoms using a mold/form configuration.

In general, the chief raw material is concentrated and preserved natural rubber latex. In addition such chemicals as acid, chlorine gases, alkalis, and corn/maize starch can be added, as is known in the art, however according to the present invention there is also added $Cu^{++}$ and $Cu^+$ in powder form.

Formers (or positive molds) are prepared through preparations that will keep the liquid latex from sticking thereto. This is done through a series of dips and treatments to the molds, as known per se in the art. The formers are then cleaned and dried and are dipped into a solution of coagulant chemicals. The coagulant forms a layer on the formers which helps to solidify latex when the formers are dipped into the latex tank.

The formers are dipped into the latex mixture, withdrawn therefrom and passed through a curing oven. The gloves and/or condoms will be vulcanized as they pass through the different areas of the oven which expose the same to temperatures ranging from about 120 to 140° C. This process cross-links the latex rubber to impart the physical qualities required.

The difference between the normal process of manufacturing a disposable glove/condom and the process of the present invention is the addition of water insoluble particles that release $Cu^{++}$ and $Cu^+$ in the raw materials.

In an especially preferred embodiment of the present invention the manufacturing process is varied in order to produce a multi-layered hydrophilic polymeric material wherein at least one of the layers is provided with water-insoluble particles that release both $Cu^{++}$ and $Cu^+$ which are directly and completely encapsulated within said hydrophilic polymeric material and a second layer is substantially free of such water-insoluble particles.

As is known, the process for the production of products from natural latex or nitrile begins with the naturally sapped or synthesized base compound. The properties of the film created from the compound, such as hardness, flexibility, toughness, adhesion, color retention, and resistance to chemicals, depends on the composition of the plastic and the additives that create different cross-linked polymers. Currently, most of these additives use a zinc cross linkage mechanism.

As is further known, copper will always displace zinc. However, the chemical qualities of copper do not allow the same linkage as zinc and are usually much weaker. Copper bonds in latex are very weak and will always create quickly biodegradable films thereby resulting in latex films having reduced structural integrity.

As described hereinbefore and as is known, a common technique used in the creation of the film after the mixture of the latex with the proper additives in the form of e.g. a glove is the molding of the latex on a hand shaped figure. In order to control the dipping of the latex from the hand model, the model is treated with a calcium nitrate/calcium carbonate coagulation of the raw materials which are then cured and cross-linked through heat and water removal. The coagulation is so quick and thorough that even after a dip of only a few seconds the mold is removed from the liquid latex and no dripping occurs. This dip in the latex is the creation of the actual glove. At that point, the glove goes through a series of ovens which cure the glove.

Normally, there is a finite limit to the thickness of the glove based on the limited effect of the calcium compounds and viscosity of the latex solution. It has now been surprisingly found according to the present invention that it is possible to extend the permeability of the calcium compounds into more than one layer, provided the layers were relatively thin.

A highly diluted latex solution (about 70% water) was prepared to which a copper powder was added. The mold was run through the calcium compounds and then run through the diluted latex. It was observed than an even thin layer was created on the mold. The mold was then placed in the normal latex bath for the normal designated time. It was surprisingly found that the mold had no problem in picking up and holding the same amount of latex as the molds which had not seen the latex/copper solution.

What was yielded was a glove with the physical characteristics of a conventionally manufactured latex glove. The glove, after curing was turned inside out, yielding a thin biologically active layer on the outside and a conventional latex glove on the inside. It is impossible to distinguish between the two layers of the glove. In order to make sure the layers were distinct a dye stuff was added to one layer and a color differentiation between the two layers was obvious.

To further test the limits of the calcium compounds and their effect on the latex, this same trial was done again but using 3 dips. The first and third dips were copper/latex and the middle dip was a conventional latex dip. A three layer glove was created that was slightly thicker than a normal glove but again, impossible to differentiate from a normal glove.

In physical testing, the end products showed all the physical characteristics of a conventional glove but showed effective biocidal and anti-viral qualities.

It will thus be realized that using this novel manufacturing process, it is possible to produce multi-layer hydrophilic polymeric materials such as gloves, condoms, tubes, sheaths, bags, etc. wherein the structural integrity is provided by the layer which has not been treated to incorporate copper therein, while the anti-viral properties are provided by a thin outer layer, a thin inner layer, or both, which thin layers have water-insoluble particles that release both $Cu^{++}$ and $Cu^+$ directly and completely encapsulated within said thin hydrophilic polymeric material.

Thus in especially preferred embodiments of the present invention there is now provided a device for the inactivation of a virus brought in contact therewith wherein said device is in the form of a nipple or nipple shield formed from a hydrophilic polymeric material, or in the form of a bag formed from a hydrophilic polymeric material or in the form of a tube formed from a hydrophilic polymeric material or in the form of a condom formed from a hydrophilic polymeric material or in the form of a diaphragm formed from a hydrophilic polymeric material or in the form of a glove formed from a hydrophilic polymeric material and wherein in each of said devices said hydrophilic polymeric material is a multi-layered polymeric material comprising at least one layer provided with water-insoluble particles that release both $Cu^{++}$ and $Cu^+$ which are directly and completely encapsulated within said hydrophilic polymeric layer and a second hydrophilic polymeric layer which is substantially free of such water-insoluble particles.

While the invention will now be described in connection with certain preferred embodiments in the following examples and with reference to the attached figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

IN THE DRAWINGS

Figure 2:
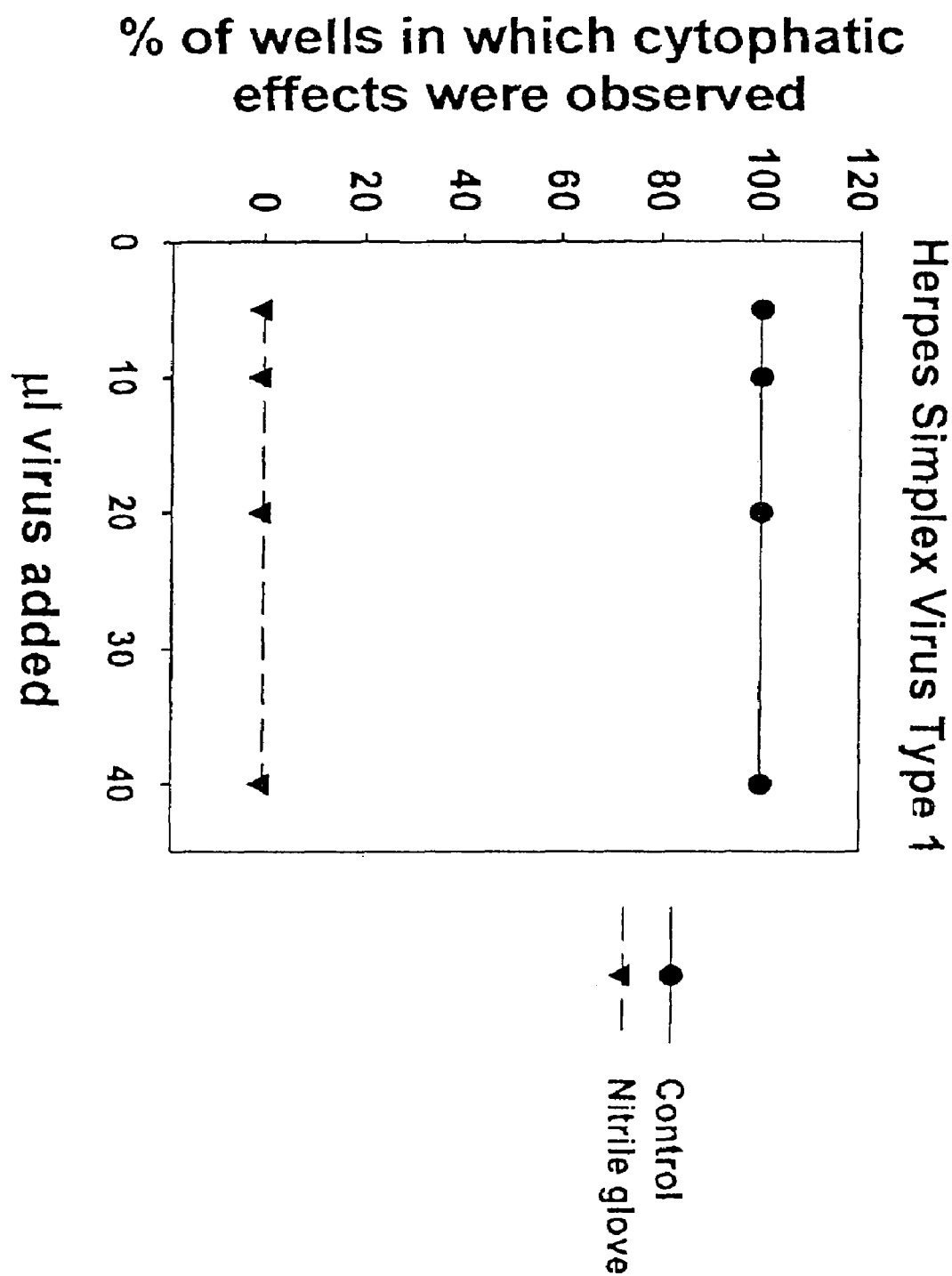

FIG. 1 is a graphical representation of the results of a comparative test of HIV-1 inhibition; and FIG. 2 is a graphical representation of the results of a comparative test of Herpes Simplex Virus Type 1 inhibition.

EXAMPLE 1 a) An amount of copper oxide powder was produced through a reduction oxidation process as known per se and as described in the aforementioned prior art. In this production formaldehyde was used as the reductant. The resulting powder was a dark brown color indicating a mixture of cupric and cupous oxides.

b) The powder was allowed to dry and was milled down to a particle size of about 4 microns.

c) An amount of bi-component latex was mixed and heated at a temperature of about 150° C. so that it was in a liquid state ready for molding.

d) Three samples were made containing 1%, 2% and 3% by weight of the powder within the latex. More specifically, in sample 1, 1 gram of powder was added to 100 grams of the heated latex slurry, in sample 2, 2 grams of powder were added to 100 grams of the heated latex slurry, and in sample 3, 3 grams of powder were added to 100 grams of the heated latex slurry e) The resulting slurry was then molded to form a plurality of latex bags.

With regard to the procedure described in Example 1, as will be realized the same system is applicable to any molding or extrusion process since the water insoluble copper containing compounds are added at the slurry stage. Thus, since the copper compounds are added at this stage of production any product can be made through molding or extrusion including but not limited to gloves, tubes, sheaths, bags, nipple shields, condoms, diaphragms or any desired product.

It is to be noted that the only limitation is that the particle size of the copper compounds must be small enough so as not to disturb the flow of the slurry through extrusion machinery which is the reason for the use of a particle size of about 4 microns in the above process. It is further to be noted that even with the addition of 3% by weight of copper compounds to the latex slurry, there was no discernible difference in the viscosity of the slurry further confirming the versatility of the invention.

The finished product was placed under an electron microscope for observation. No copper oxide particles could be identified by sight or through spectrographic readings on the surface of the molded product which was different than the observations made when the same process was carried out using a polyester polymer.

In the case of a polyester fiber, it was noted that the particles of the copper oxide compound, even when milled down to a 2 micron size, still protruded from the surface of the polymer.

EXAMPLE 2

A plurality of bags prepared according to Example 1 were sent to the Ruth Ben-Ari Institute of Clinical Immunology and AIDS Center at the Kaplan Medical Center in Israel for testing.

Method: Aliquots of medium containing HIV were placed in UV sterile Cupron copper-containing latex bags or in UV sterile latex bags not containing copper. Virus stocks that were not exposed to any material served as positive controls for infectivity. As a negative control for viral activity, medium without any virus was placed in the Cupron copper containing bags. After 20 minutes of incubation at room temperature, 50 µl drops from each of the bags were mixed with 40 µl fresh medium containing 10% fetal calf serum (FCS), and each mixture was added to target cells in 1 ml medium containing 10% FCS. The virus-cell mixtures were then incubated in 24 well plates in a $CO_2$ humidified incubator at 37° C. After four days of incubation the amount of virus present per well was quantified.

Results: No viral infectivity was measured in the medium spiked with virus and exposed to the Cupron copper containing bags or in the non-spiked medium, while the viral infectivity of the medium containing virus and exposed to a latex bag, which did not contain copper, were similar to that of the stock virus used.

Conclusion: The Cupron copper-containing latex bags deactivated the virus.

Thus the results of Example 2 conclusively prove that a device according to the present invention is effective for inactivating viruses in fluids brought in contact therewith and thus e.g. blood storage bags according to the present invention can assure that blood stored therein will not transmit a virus to a recipient of said blood.

EXAMPLE 3

Steps a, b and c of Example 1 are repeated however while in a conventional latex solution the normal water content is about 30-35%, the amount of water in the solution was doubled so that it was 70% water and 30% latex.

To the 70% water/30% latex solution there was added 3% (calculated based on the weight of the latex) a cuprous oxide compound comprising a mixture of cuprous and cupric oxide powders wherein said powders were formed of particles of up to 2 microns in diameter. The powder was stirred into the latex solution and kept agitated to assure that it remained homogenous. The process was performed at room temperature.

A ceramic model of a hand was dipped into a calcium nitrate/calcium carbonate solution sufficient to wet the model. The model was then dipped for up to 5 seconds in the diluted copper/latex solution. The model was spun on its axis to remove excess chemicals through centrifugal force. The model was then returned to the normal production line where it was dipped in the conventional latex and allowed to go through normal production.

The glove after curing was then turned inside out and was found to have a thin biologically active layer on the outside having a thickness of about 80-100 microns and an inner layer having a thickness of about 1000-1200 microns.

EXAMPLE 4

Gloves prepared according to Example 3 were tested for their anti-viral properties wherein a double-layered natural latex glove as well as a double-layered nitrile glove were prepared and tested.

EXAMPLE 4A

Inhibition of HIV-1 Clade A

150 µl aliquots of HIV-1 Clade A stock virus were placed on top of a series of double-layered Cupron latex gloves and on top of a series of double-layered Cupron Nitrile gloves for 20 minutes at room temperature. As control, 150 µl of virus, which was not exposed to the gloves, was incubated for 20 minutes at room temperature. The various virus aliquots were then sequentially diluted (1:3 dilutions) in medium and the dilutions were added to MT-2 cells (T-cells susceptible to HIV-1 infection), done in quadruplicates. The presence of syncytia formation, (indicative of virus infection) in the MT-2 cells was determined after 7 days of culture at 37° C. in a moist incubator by an inverted microscope. This served as the basis to calculate the 50% Tissue Culture Infectious doses ($TCID_{50}$) as set forth in the Table in FIG. 1.

EXAMPLE 4B

Inhibition of HSV-1

150 µl aliquots of Herpes Simplex Virus Type 1 (HSV-1) aliquots were placed on top of a series of double-layered Cupron Nitrile gloves for 20 minutes at room temperature. As control, 150 µl of virus, which was not exposed to the glove, was incubated for 20 minutes at room temperature. Then, 5, 10, 20 or 40 µl of these viral aliquots were added to 293 cells (cells susceptible to HSV-1) grown in 1 ml culture medium (done in duplicates). After 2 days of culture at 37° C. in a moist incubator the cytopathic effect of the virus (formation of plaques) was examined by an inverted microscope). As can be seen in FIG. 2 appended hereto, the gloves according to the present invention were effective at all of the viral concentrations to inhibit the same.

From the above Examples it is clear that the hydrophilic polymeric material and the devices according to the present invention incorporating the same possess antiviral properties and their use for blood storage and transfer as well as for protective gloves, condoms, etc. provides a major advantage over the products presently available on the market and can be a major boon for preventing viral transfer.

EXAMPLE 5

In order to further test the limits of the calcium compounds and their effect on the latex, the procedure of Example 3 was repeated however using 3 dips. The first and third dips were copper/latex and the middle dip was a conventional latex dip. A three layer glove was created that was slightly thicker than a normal glove but again, impossible to differentiate from a normal glove.

In physical testing, the end products showed all the physical characteristics of a conventional glove but showed effective biocidal and anti-viral qualities.

The following Tables demonstrate that the structural integrity of a product according to the present invention is maintained when producing a double or triple layered glove as opposed to merely introducing the water insoluble particles into a single layer product.

In Table 1 there is shown the testing of a normal latex glove wherein the load peak is in the range of about 8.

In Table 2 there is shown the testing of a single layer latex glove having 1% copper oxide incorporated therein wherein the load peak is reduced to values between 6.5 and 7.7.

In Table 3 there is shown the testing of a triple layer latex glove according to the present invention wherein while one glove showed a load peak of 7.4, the other three gloves tested showed load peaks of between 8.6 and 10.1.

TABLE 1

TENSILE TEST REPORT

TEST NO.: SAMPLE  Test: RUBBER TENSILE
PRO. DATE:  Test Type: Tensile
PRO. SHIFT: DAY  Date: Dec. 31, 2003
COM.BA.NO.:  Test Speed: 500.00 mm/min
STYLE: SLAPT  Sample Length: 070.0 mm
R.P.M.:  Sample Type: RECTANGULAR
PLANT No.  Pre-Tension: OFF
TESTED BY: DESAPRIYA
Comments: CONTROL SAMPLE

| Test No. | Width mm | Thick. mm | Stress @ Peak N/mm² | Strain @ Peak % | Stress @ 500% N/mm² | Load @ Peak N |
|---|---|---|---|---|---|---|
| 1 | 3.0000 | 0.1350 | 20.385 | 777.42 | 5.9197 | 8.2560 |
| 2 | 3.0000 | 0.1350 | 20.842 | 745.24 | 6.5187 | 8.4410 |
| Min. | 3.0000 | 0.1350 | 20.385 | 745.24 | 5.9197 | 8.2560 |
| Mean | 3.0000 | 0.1350 | 20.614 | 761.33 | 6.2192 | 8.3485 |
| Max. | 3.0000 | 0.1350 | 20.8.42 | 777.42 | 6.5187 | 8.4410 |
| S.D. | 0.0000 | 0.0000 | 0.323 | 22.76 | 0.4236 | 0.1309 |

TABLE 2

TENSILE TEST REPORT

TEST NO.: SAMPLE  Test: RUBBER TENSILE
PRO. DATE:  Test Type: Tensile
PRO. SHIFT: DAY  Date: Dec. 31, 2003
COM.BA.NO.:  Test Speed: 500.00 mm/min
STYLE: LATEX  Sample Length: 070.0 mm
R.P.M.:  Sample Type: RECTANGULAR
PLANT No.:  Pre-Tension: OFF
TESTED BY: DESAPRIYA
Comments: LB 1

| Test No. | Width mm | Thick. mm | Stress @ Peak N/mm² | Strain @ Peak % | Stress @ 500% N/mm² | Load @ Peak N |
|---|---|---|---|---|---|---|
| 1 | 3.0000 | 0.1150 | 20.038 | 799.49 | 5.1830 | 6.9130 |
| 2 | 3.0000 | 0.1250 | 20.251 | 823.34 | 4.6917 | 7.5940 |
| 3 | 3.0000 | 0.1250 | 20.749 | 807.36 | 4.9371 | 7.7810 |
| 4 | 3.0000 | 0.1200 | 18.303 | 779.42 | 4.9384 | 6.5890 |
| Min. | 3.0000 | 0.1150 | 18.303 | 779.42 | 4.6917 | 6.5890 |
| Mean | 3.0000 | 0.1213 | 19.835 | 802.40 | 4.9375 | 7.2193 |
| Max. | 3.0000 | 0.1250 | 20.749 | 823.34 | 5.1830 | 7.7810 |
| S.D. | 0.0000 | 0.0048 | 1.064 | 18.25 | 0.2006 | 0.5618 |

TABLE 3

TENSILE TEST REPORT

TEST NO.: LA 1 3 DIP  Test: RUBBER TENSILE
PRO. DATE: Feb. 1, 2004  Test Type: Tensile
PRO. SHIFT: DAY  Date: Feb. 1, 2004
COM.BA.NO.:  Test Speed: 500.00 mm/min
STYLE:  Sample Length: 070.0 mm
R.P.M.:  Sample Type: RECTANGULAR
PLANT No.:  Pre-Tension: OFF
TESTED BY: RUVINI
Comments: TUMBLING AT 70 C.

| Test No. | Width mm | Thick. mm | Stress @ Peak N/mm² | Strain @ Peak N | Stress @ 500% N/mm² | Load @ Peak N |
|---|---|---|---|---|---|---|
| 1 | 3.0000 | 0.1300 | 19.082 | 725.24 | 6.9383 | 7.442 |
| 2 | 3.0000 | 0.1900 | 17.753 | 753.06 | 5.2983 | 10.119 |
| 3 | 3.0000 | 0.1800 | 17.367 | 747.57 | 5.3093 | 9.378 |
| 4 | 3.0000 | 0.1800 | 15.967 | 757.87 | 5.0437 | 8.622 |
| Min. | 3.0000 | 0.1300 | 15.967 | 725.24 | 5.0437 | 7.442 |
| Mean | 3.0000 | 0.1700 | 17.542 | 745.94 | 5.6474 | 8.890 |
| Max. | 3.0000 | 0.1900 | 19.082 | 757.87 | 6.9383 | 10.119 |
| S.D. | 0.0000 | 0.0271 | 1.282 | 14.42 | 0.8693 | 1.143 |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A multi-layered hydrophilic polymeric material for inactivation of a virus, wherein said polymeric material comprises
   a first hydrophilic polymeric layer having particles encapsulated within, wherein said particles consist essentially of copper oxide, and wherein said particles release both $Cu^{++}$ and $Cu^+$ and
   a second hydrophilic polymeric layer which is substantially free of copper oxide particles.

2. A multi-layered hydrophilic polymeric material for inactivation of a virus according to claim 1 wherein said particles are of a size of between about 1 and 10 microns.

3. A multi-layered hydrophilic polymeric material for inactivation of a virus according to claim 1 wherein said particles are present within said hydrophilic material in a concentration of about 1 to 3 w/w %.

4. A multi-layered hydrophilic polymeric material for inactivation of a virus according to claim 1, wherein said first hydrophilic polymeric layer comprises a material selected from the group consisting of latex, nitrile, acrylics, polyvinyl alcohol and silastic rubber.

5. A multi-layered hydrophilic polymeric material for inactivation of a virus according to claim 4, wherein said first hydrophilic polymeric layer and said second hydrophilic polymeric layer are formed of the same polymeric material.

6. A hydrophilic polymeric material for inactivation of a virus according to claim 1 wherein said polymeric material is in the form of a film.

7. The multi-layered hydrophilic polymeric material of claim 1, wherein copper oxide is the sole antiviral component therein.

8. The multi-layered hydrophilic polymeric material of claim 1, wherein the first hydrophilic polymeric layer is latex.

9. The multi-layered hydrophilic polymeric material of claim 8, wherein the second hydrophilic polymeric layer is latex.

10. The multi-layered hydrophilic polymeric material of claim 1, that comprises a third hydrophilic polymeric layer.

11. The multi-layered hydrophilic polymeric material of claim 10, wherein said third hydrophilic polymeric layer comprises particles consisting essentially of copper oxide.

12. The multi-layered hydrophilic polymeric material of claim 11, wherein said third hydrophilic polymeric layer lies between said first and said second layers.

13. The multi-layered hydrophilic polymeric material of claim 12, wherein at least one of said layers is latex.

14. The multi-layered hydrophilic polymeric material of claim 13, wherein said first, second and third layers are latex.

* * * * *

(12) EX PARTE REEXAMINATION CERTIFICATE (9194th)
United States Patent
Gabbay

(10) Number: US 7,364,756 C1
(45) Certificate Issued: Aug. 14, 2012

(54) ANTI-VIRUS HYDROPHILIC POLYMERIC MATERIAL

(75) Inventor: Jeffrey Gabbay, Jerusalem (IL)

(73) Assignee: The Cupron Corporation, New York, NY (US)

Reexamination Request:
No. 90/011,427, Feb. 14, 2011

Reexamination Certificate for:
Patent No.: 7,364,756
Issued: Apr. 29, 2008
Appl. No.: 10/772,890
Filed: Feb. 4, 2004

Related U.S. Application Data

(63) Continuation-in-part of application No. 10/752,938, filed on Jan. 6, 2004, now abandoned.

(30) Foreign Application Priority Data

Aug. 28, 2003 (IL) .................................................. 157625

(51) Int. Cl.
*A61K 33/34* (2006.01)
*A61K 31/74* (2006.01)
*A01N 25/34* (2006.01)

(52) U.S. Cl. ...................... 424/635; 424/404; 424/78.08

(58) Field of Classification Search ........................ None
See application file for complete search history.

(56) References Cited

To view the complete listing of prior art documents cited during the proceeding for Reexamination Control Number 90/011,427, please refer to the USPTO's public Patent Application Information Retrieval (PAIR) system under the Display References tab.

*Primary Examiner*—Johnny F Railey

(57) ABSTRACT

The invention provides a method for imparting antiviral properties to a hydrophilic polymeric material comprising preparing a hydrophilic polymeric slurry, dispersing an ionic copper powder mixture containing cuprous oxide and cupric oxide in said slurry and then extruding or molding said slurry to form a hydrophilic polymeric material, wherein water-insoluble particles that release both $Cu^{++}$ and $Cu^+$ are directly and completely encapsulated within said hydrophilic polymeric material.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 11 are determined to be patentable as amended.

Claims 2-10 and 12-14 dependent on an amended claim, are determined to be patentable.

1. A multi-layered hydrophilic polymeric material for inactivation of a virus, wherein said polymeric material comprises a first hydrophilic polymeric layer having particles *completely* encapsulated within, wherein said particles consist essentially of copper oxide, and wherein said particles release both $Cu^{++}$ and $Cu^+$, and a second hydrophilic polymeric layer which is substantially free of copper oxide particles.

11. The multi-layered hydrophilic polymeric material of claim 10, wherein said third hydrophilic polymeric layer comprises particles [consisting] *completely encapsulated within and said particles consist* essentially of copper oxide.

* * * * *